(12) United States Patent
Tarver, III et al.

(10) Patent No.: US 6,580,068 B1
(45) Date of Patent: Jun. 17, 2003

(54) METHOD AND APPARATUS FOR TIME DISPERSIVE SPECTROSCOPY

(75) Inventors: Edward E. Tarver, III, Livermore, CA (US); William F. Siems, Spokane, WA (US)

(73) Assignee: Sandia Corporation, Livermore, CA (US)

( * ) Notice: Subject to any disclaimer, the term of this patent is extended or adjusted under 35 U.S.C. 154(b) by 0 days.

(21) Appl. No.: 09/351,081

(22) Filed: Jul. 9, 1999

(51) Int. Cl.[7] ............................................... B01D 59/44
(52) U.S. Cl. ........................ 250/286; 250/282; 250/287; 250/281; 250/498; 364/498
(58) Field of Search .................. 250/286, 282, 250/287, 281–300; 364/498

(56) References Cited

U.S. PATENT DOCUMENTS 4,633,083 A * 12/1986 Knorr et al. ............... 250/282
4,707,602 A * 11/1987 Knorr ......................... 250/282
5,719,392 A * 2/1998 Franzen ...................... 250/282

OTHER PUBLICATIONS

F. J. Knorr, R. L. Eatherton, W. F. Siems, an H. H. Hill, Jr., Fourier Transform Ion Mobility Spectrometery, Anal. Chem. 1985, 57, 402–408.

* cited by examiner

Primary Examiner—John R. Lee
Assistant Examiner—Zia R Hashmi
(74) Attorney, Agent, or Firm—Timothy P. Evans

(57) ABSTRACT

Methods and apparatus are described for time dispersive spectroscopy. In particular, a modulated flow of ionized molecules of a sample are introduced into a drift region of an ion spectrometer. The ions are subsequently detected by an ion detector to produce an ion detection signal. The ion detection signal can be modulated to obtain a signal useful in assaying the chemical constituents of the sample.

17 Claims, 7 Drawing Sheets

METHOD AND APPARATUS FOR TIME DISPERSIVE SPECTROSCOPY

STATEMENT OF GOVERNMENT INTEREST

The United States Government has rights in this invention pursuant to Department of Energy Contract No. DE-AC04-94AL85000 with Sandia Corporation.

BACKGROUND OF THE INVENTION

This invention relates generally to the field of time dispersive spectroscopy. More particularly, methods and apparatus are provided for determining the chemical constituents of a sample predicated on separating the constituents on the basis of their a differing velocities. The present invention includes time dispersive devices such as ion mobility spectrometers (IMS), plasma chromatography, time-of-flight (TOF) mass spectrometers, capillary gas chromatographs and the like.

Presently, there are four methods of time dispersive spectrometry. The first is the "single scan" method which involves opening an entrance gate for a short period of time to admit ions into a drift region of a spectrometer. The entrance gate is typically left open for approximately 0.2 milliseconds before it is closed thereby blocking further ions from entering the drift region. The pulse of ions admitted during the period the entrance gate is open move down the drift region under the force of an electric field and countercurrent to a drift gas. In the single scan method there is no exit gate and the ions strike directly onto an ion detector. The ion detector is connected to an oscilloscope which is used to monitor the output signal of the ion detector. The single scan method suffers from high noise levels in the detector output signal and accordingly cannot be used for high resolution chromatographic separations.

The second method of time dispersive spectroscopy is termed the "signal averaging" method. The signal averaging method again involves opening the entrance gate for a short period of time to allow a pulse of ions to pass into the drift region and be propelled therethrough under the force of the electric field. The ions again strike directly upon the ion detector, as in the single scan method. In the signal averaging method, many repetitions of single scans are performed and recorded, such as with a computer. Five hundred to 1,000 repetitions are often required to provide statistically acceptable signal to noise levels. Such numerous repetitions typically require a minimum of 10 to 20 seconds to perform thereby rendering the method unacceptable for high resolution chromatographic separation of sample constituents on an on-line basis.

The third method of time dispersive spectroscopy is termed the "moving second gate" method. Such method is used with ion mobility spectrometers having an exit gate which is located at the end of the drift region prior to the ion detector. A pulse of ions are admitted through the entrance gate and propelled through the drift region under the force of the electric field. The second or exit gate positioned at the end of the drift region selectively opens for a short period of time usually equal to the time the entrance gate is opened. The time delay between opening of the entrance gate and subsequent opening of the exit gate thus allows only ions having transit times approximately equal to such time delay to pass through the exit gate and onto the ion detector. The strength of the measured signal indicates the quantity of ions having such transit time. The time delay between the opening of the entrance gate and the opening of the exit gate is varied over a range of relevant transit times and a large number of experimental ion pulses are needed in order to generate acceptable data indicating ion quantity (signal strength) as a function of transit time. Because of the large number of different delay times which must be tested, the amount of time necessary to test the full spectrum of transit times with sufficient specificity, accuracy, and to obtain acceptable signal to noise levels thus requires testing for a minimum of one or two minutes. Thus, the moving second gate method is also not acceptable for analyzing constituents on an on-line basis, especially if the amount of sample material is limited.

The fourth method of time dispersive spectroscopy is known as Fourier transform ("FT") method as described by Knorr, et al in U. S. Pat. 4,633,083 and "Fourier Transform Ion Mobility Spectrometer" by Knorr et al in *Anal Chem.* Vol. 57, 402–406 (1985), both of which are incorporated by reference herein. In the FT method, the ions are admitted into a drift region in pulses by opening an entrance gate for variable short periods of time termed gate open or ion admission periods. Consideration of only those ions exiting the drift region during gate open periods can be accomplished using an exit gate which simultaneously opens and closes with the opening and closing of the entrance gate, thereby allowing ions to be detected which exit during the entrance gate open periods and excluding ions exiting during complementary entrance gate closed periods. Simultaneous opening and closing of the entrance and exit gates is controlled by a gating function over a range of frequencies to produce associated ranges of times for the gate open periods and gate closed periods. Only ions which exit the drift region during the entrance gate open periods are considered in the subsequent analysis. Data is recorded in the form of the ion detection signal as a function of the variable gate frequency. For each type of ion there are a series of maxima in the ion detection signal when the ion pulses are in phase with the gating function. Correspondingly, for each ion there are a series of minima in ion detection signal when the ion pulses are out of phase with the gating function. The ion pulses are thus said to interfere or form an interference function with the gating function. Data in the form of ion detection signal as a function of frequency can thus be plotted as an interference function or interferogram displaying such maxima and minima. The interference function contains information on the quantity of ions having various transit times. This information can be transformed from the frequency domain to the time domain using a suitable mathematical transform such as a Fourier transform, or "FT".

There are two clear advantages of FT method compared to the other methods of operation previously described. First, because the duty cycle of the FT method is 25 times that of the single scan method, the FT method offers up to five times the signal to noise ratio(S/N). Second, the peak asymmetries due to reactions in the drift tube simply disappear in the FT method. This occurs because the FT method uses a constant frequency difference between the ion-carried chirp and the second gate to generate a constant beat frequency. Ions that react during their transit of the drift region have no well-defined drift time and give incoherent signals at the second gate, adding only to the DC signal level and random background noise.

Nevertheless, there remain at least three problems with the ET method of time dispersive spectroscopy. First, in addition to different gating electronics associated with the spectrometer, the FT method has required a drift tube of basically different construction than most of the more conventional time dispersive devices making it difficult for users to use the method. Secondly, it has been difficult to make direct comparisons of actual relative performance of the FT method with existing ion mobility spectra because the differing designs have required either awkward, time consuming, and contamination producing component interchanges or use of drift tubes having two gates and an aperture grid, with the attendant signal loss due to a third screen. Partly for these reasons, there has been no S/N comparisons which might encourage wider adoption of the FT method. Thirdly, having two physical gates within the drift region reduces the duty cycle from a theoretical maximum of 50% to 25% and the potential enhancement of S/N from seven to five.

Additionally, none of the existing four methods of time dispersive spectroscopy described above make the most efficient use of the available ions. Typical entrance gate pulse durations of 0.2 milliseconds with recurrent pulses every 20 milliseconds allow only one percent of the available ions from the sample to pass into the drift region. This small proportion of the available ions admitted into the drift region is further reduced in the moving second gate method by the selective opening and closing of the exit gate for approximately similar periods of time. This results in an average of only one percent of the ions admitted through the entrance gate passing through the exit gate and onto the ion detector. The resulting 1.0 percent utilization of available ions allows only a relatively weak signal to be developed at the ion detector, thus causing a poor signal to noise ratio. This requires that multiple scans be averaged to achieve adequate signal-to noise.

The present invention provides novel method and apparatus for chemical analysis by time dispersive spectrometry. Unlike previous methods and apparatus, the present invention does not require the use of two physical gates within drift region of the time dispersive spectrometer. More specifically, the present invention employs modulation of the detection signal and an FT mode of operation without modifying conventional time dispersive devices to include a second physical gate. Consequently, the results obtained by the present invention are directly comparable to single gated time dispersive devices. Moreover since only a single physical gate is employed, the present invention is able to achieve higher signal-to-noise ratios than current FT devices employing two physical gates as well as better utilize the amount of sample available.

SUMMARY OF THE INVENTION

The present invention provides novel methods and approaches for identifying chemical constituents of a multi-component sample using time dispersive spectrometry. In particular, the present invention more effectively utilizes limited sample materials available for analysis. Additionally, the present invention achieves higher signal to noise ratios resulting in more accurate analysis of chemical constituents of a sample.

In one embodiment of the present invention, the flow of an ionized sample into a drift region of a time dispersive spectrometer is modulated; ions traversing the drift region of a time dispersive device are detected and an ion detection signal is obtained; and the ion detection signal is modulated to obtain a frequency domain representation of the chemical constituents of the sample. Further, the frequency domain representation of the chemical constituents can be transformed into a time-domain representation of the chemical constituents of the sample, both qualitative and quantitative analyses of the constituents can be performed on the modulated ion detection signal.

In another embodiment of the invention, a time dispersive spectrometer includes a first physical gate for controlling the flow of an ionized sample into a drift region of the time dispersive spectrometer and an ion detector for producing an ion detection signal after the ions have traversed the drift region. The time dispersive spectrometer further includes a modulator for controlling both the flow ions past the first physical gate and modulating the ion detection signal to obtain a frequency domain representation of the chemical constituents of the sample. The apparatus further includes means for transforming the frequency domain representation into a time domain representation of the constituents of the sample.

The apparatus further includes means for transforming the frequency domain representation into a time domain representation of the constituents of the sample.

DETAILED DESCRIPTION OF THE INVENTION

Figure 1:
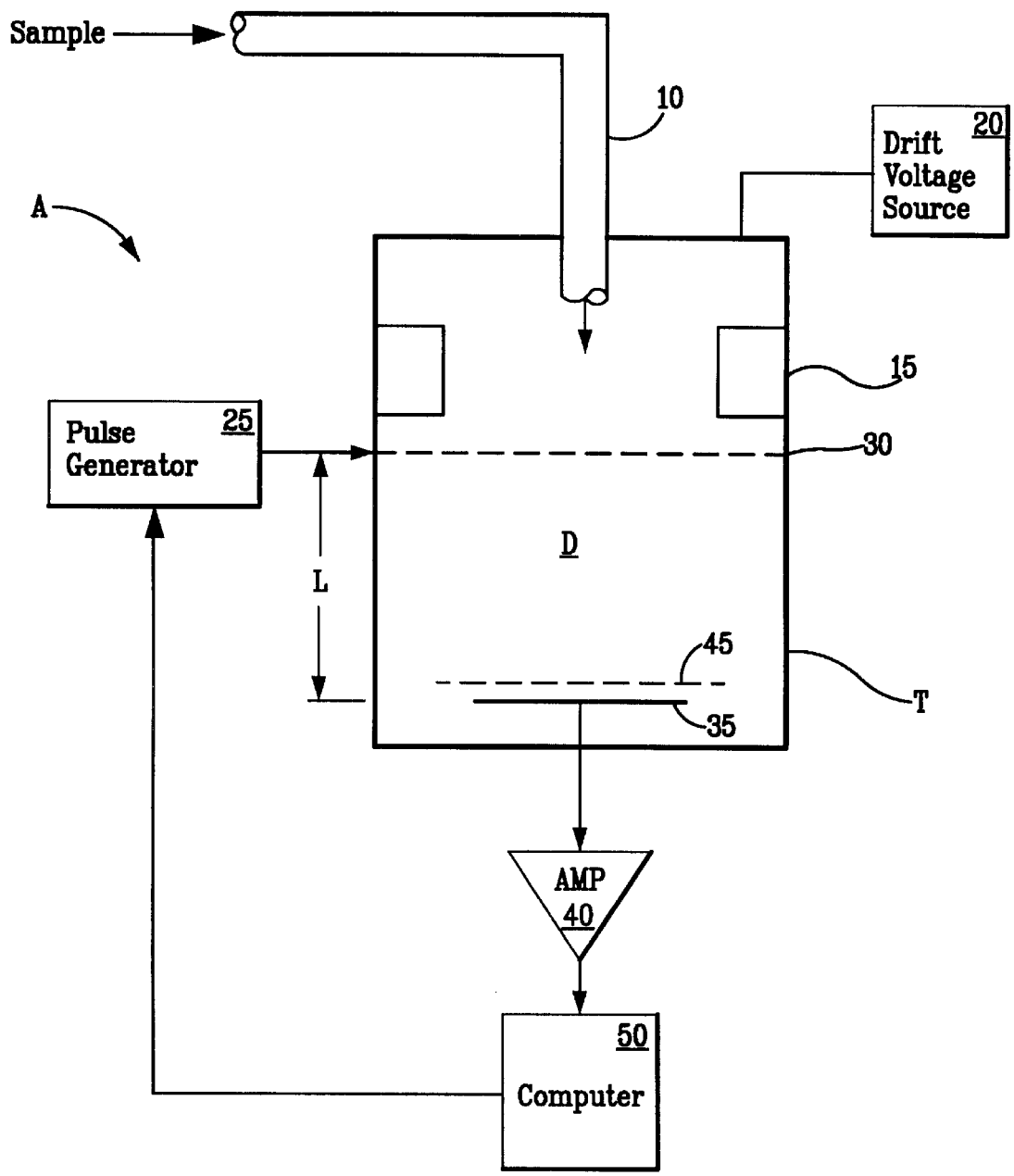
FIG. 1 is a schematic diagram of a conventional time dispersive ion mobility spectrometer.

The present invention provides novel methods and apparatus for both qualitative and quantitative chemical analysis of constituents of a sample employing time dispersive spectrometry. Unlike existing FT spectroscopic devices, the present invention does not require the use of two physical gates within the drift region of the spectrometer. More specifically, the present invention modulates of the ion detection signal and provides an FT mode of operation without modifying conventional time dispersive devices to include a second or exit gate. Consequently, the results obtained by the present invention are directly comparable to single gated time dispersive devices. Moreover since only a single physical gate is employed, the present invention is able to achieve higher signal-to-noise ratios than present FT spectroscopic devices employing two physical gates as well as better utilize the sample provided.

To better understand the present invention, the following introductory discussion of the operation of time dispersive spectrometers is provided. Looking first to FIG. 1, a conventional time-dispersive ion mobility spectrometer A is depicted. Typical of such time dispersive devices is the Ionscan 400 ion mobility spectrometer manufactured by Barringer Instruments, Inc., Warren, N.J. In particular, the spectrometer A includes an inlet sample line 10 for introducing a sample to be ionized, an ionizer 15, a drift voltage source 20, a pulse generator 25 to control the opening and closing of gate 30 and thus regulate the flow of ions into a drift region D of drift tube T, an ion detector 35, an amplifier 40, an aperture grid 45, and computer 50.

The first step of ion mobility spectrometry is to pass a sample through the ionizer 15 to produce electrically charged molecules usually called ions. These ions are allowed to enter the drift region D provided with an electric field developed by drift voltage source 20 which causes the charged ions to move through the drift region D. The ion detector 35 is provided at or near the opposite end of the drift region D to detect ions which have traversed therethrough.

The drift region D is provided with a steady flow of a drift gas (not shown) flowing opposite to the direction that the ions travel under the force of the electric field. The time which it takes for ions to travel the distance L from the entrance gate 30 across the drift region D to the ion detector 35 depends upon the mass, geometry and size of the ion, its electrical charge, and the distance which must be traveled. Other factors can also effect the velocity or mobility of the ions in the drift region D to produce varying transit times which are characteristic or indicative of the types of ions present.

In the usual, or "normal," mode of operation of ion mobility spectrometer A, illustrated schematically in FIG. 1, ions of a sample are introduced as a plug of brief duration, often by means of an entrance gate 30 (e.g., a Bradbury-Nielsen shutter grid or a sample injection loop in chromatography.) The constituents of the sample separate ski as the lower velocity constituents lag behind those of higher velocity. The separated constituents arrive at the ion detector 35(e.g., a Faraday plate in IMS, a microchannel plate in TOF MS, or an FID in gas chromatography) where they are converted to an electrical current or voltage, which is then amplified by amplifier 40 processed by a computer-based data acquisition system 50. The resulting time-of-flight spectra and signal intensities are the bases for both quantitative and qualitative analysis of the sample.

Whenever the sample to be introduced is available in only limited amounts and/or for a limited period of time, the pulsed nature of the normal mode of operation results in substantial waste of the scarce sample material. The duty cycle of the entrance gate 30 is typically low, generally on the order of 1% or less, in order to maximize the power of the spectrometer A to resolve closely spaced peaks. Thus, 99% or more of the sample is discarded. If it was somehow possible to use this lost 99% of the sample, for example by successively directing a 1% duty cycle pulse into each of 100 separators, and then adding together the resulting 100 arrival time spectra. In this case for the sample component of each signal S would increase by a factor of 100, while the random baseline noise N would only increase by a factor of 10, so that S/N would increase by a factor of 10. While crowding 100 spectrometers together seems physically impossible, there is clearly a potential S/N benefit to be obtained from any multiplexing scheme which makes effective use of more than 1% of the sample.

Ion mobility spectrometry is a high pressure (>10 torr) technique that has proved useful in a variety of separation and trace level monitoring applications. The ion mobility spectrometer A, can be set up to operate in either the single-scan or signal averaging mode. Separation is based on the fact that an ion in a drift gas will have a characteristic velocity, $V_d$, in the presence of a constant electric field E, as given by:

$$v_d = KE \tag{1}$$

The proportionality constant K is called the mobility, and at atmospheric pressure the value of K typically lies in the range 0.5–3 $cm^2$/V sec. A major factor determining the mobility of a particular ion is its collision cross section for the drift gas, with a smaller ion having a higher mobility. The drift time of an ion, $t_d$, is related to the drift distance, L, between the gate 30 and the collector 35 and to the total voltage drop, V, over this same distance, as given by:

$$t_d = \frac{L^2}{KV} \tag{2}$$

To generate a constant electric field E, the voltage produced by the drift voltage source 20 is dropped to ground through a resistance divider (not shown), which is tapped at appropriate intermediate positions to supply reference voltages to stacked metal guard rings (not shown) defining the edge of the drift region D. The entering sample is ionized in some fashion (radioactive foil, electrospray, photoionization, etc.), and the ion mobility experiment is initiated by admitting sample ions through the gate 30, with the pulse duration being controlled by the gate controller 25.

In many time-dispersive devices, it is possible for undesired chemical reactions involving sample molecules to occur during the separation process, resulting in "fronting" of the sample peak if the product of the reaction has a higher velocity than the original sample molecule, "tailing" if the product has a lower velocity. An aperture grid 45 can be provided to prevent the ion detector 35 from responding capacitively to approaching ion swarms, and if it is not eliminated ion signals become very broad.

Figure 2A:
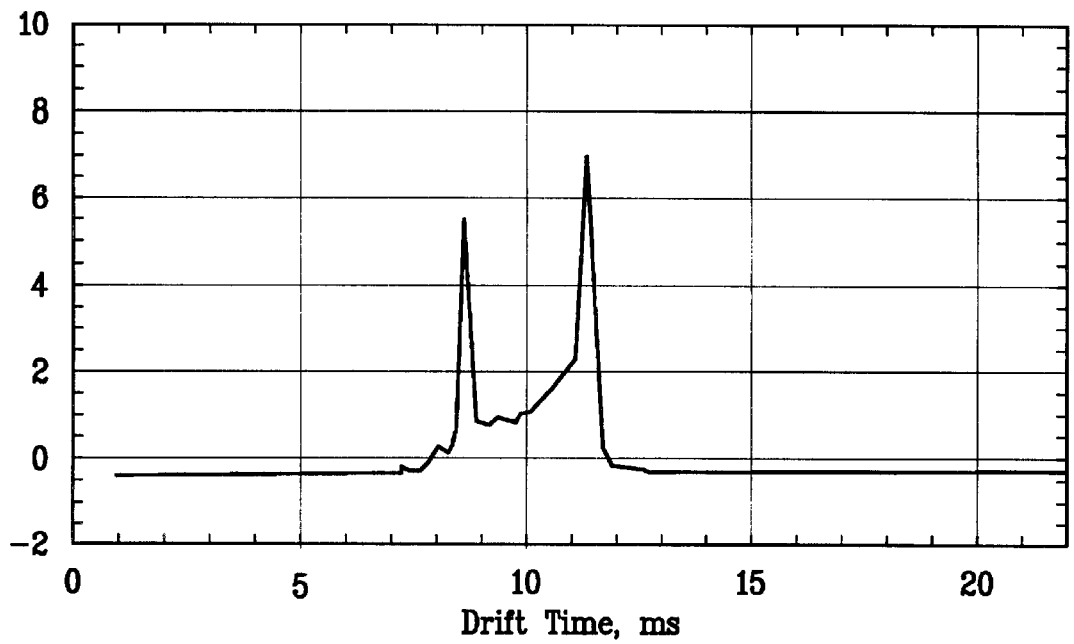
FIG. 2(a) represents a normalized time-of-flight spectra for an averaged signal acquired from a 2.0 second scan.

Usually the ion mobility experiment is repeated many times and the results averaged to increase S/N, as depicted in FIG. 2(a).

Figure 3:
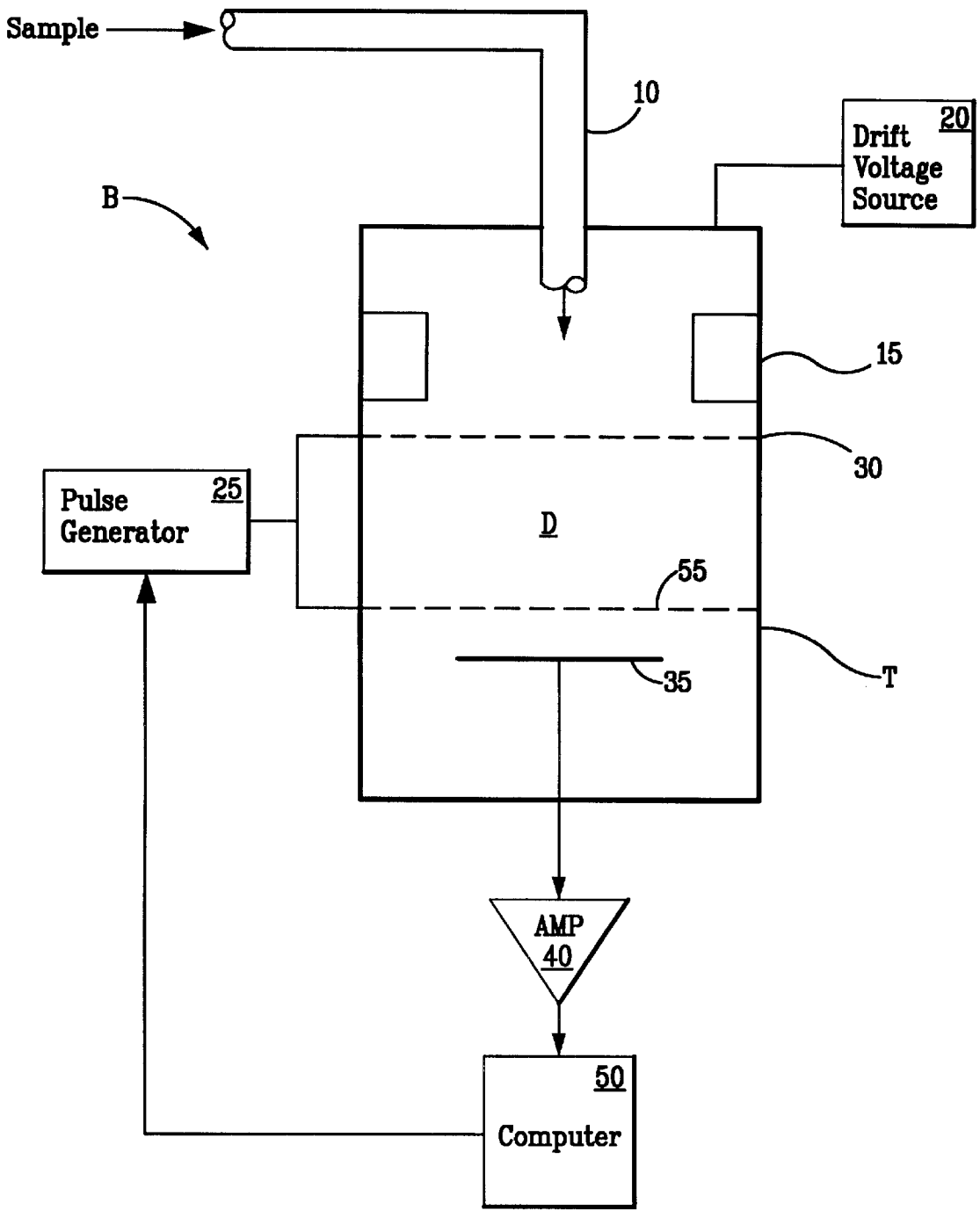
FIG. 3 is a schematic diagram of an FT ion mobility spectrometer.

Looking next to FIG. 3, the FT mode of operation, as it has generally been performed with spectrometer B, is depicted. The aperture grid 45 of spectrometer A is removed and a second or exit gate 55 is added as shown in FIG. 3. The pulse generator 25 produces a waveform called a chirp. The chirp waveform is a 50% duty cycle square wave, e(t), with a frequency that increases linearly with time:

$$e(t) = 1 \text{ for } \sin 2\pi\left(v_o + \frac{1}{2}Rt\right)t > 0 \tag{3}$$
$$= 0 \text{ for } \sin 2\pi\left(v_o + \frac{1}{2}Rt\right)t \le 0$$

where $v_0$ is the initial frequency of the chirp signal and R is the scan rate in Hz $s^{-1}$. Note that the frequency of e(t) as a function of time is given by:

$$v(t) = \frac{1}{2\pi}\frac{d\left(2\pi\left(v_0 + \frac{1}{2}Rt\right)t\right)}{dt} = v_o + Rt \tag{4}$$

and that the rate of change of v(t) is indeed RHz $s^{-1}$.

Each type of ion generated from the sample carries an image of the chirp signal waveform, translated through the drift region D at a velocity, $v_d$, characteristic of the particular ion. The ion waveform chirp arrives at exit gate 55 at $t_d$ seconds after its generation. Since exit gate 55 is also controlled by the pulse generator 25, there is a fixed frequency difference of $Rt_d$ between the chirp waveform carried by the ions and the chirp signal applied to the exit gate 55. This fixed frequency difference in turn gives rise to a constant beat frequency of $Rt_d$ Hz in the signal gathered at the ion detector 35 and digitized by the computer 50. Each ion derived from the sample gives rise to its own characteristic frequency in the digitized signal (the interferogram), and the normal ion mobility spectrum can be recovered by proper digital filtration and Fourier transformation of this interferogram. If the FT software gives an output with x axis labeled by frequency, then the drift times can be recovered by dividing all the frequencies by R.

More precisely, if e(t) represents the signal applied to exit gate 55, then the signal carried by a single ion population would be given by $e(t-t_d)$ and the remaining ion signal passing through exit gate 55 and reaching the ion detector 35 is given by the products $S(t)=e(t-t_d)c(t)$. Just as:

$$\sin a \cdot \sin b = 0.5[\cos(a-b)+\cos(a+b)] \quad (5)$$

contains a difference frequency, S(t) contains the difference frequency:

$$f = \frac{d}{2\pi dt}\cos 2\pi[(v_0 - 0.5Rt)t - (v_0 - 0.5R)t - t_d))(t - t_d)] \quad (6)$$
$$= \frac{d}{2\pi dt}co2\pi \left| v_0 t_d + Rtt_d - 0.5Rt_d^2 \right| = Kt_d$$

Of course the sum frequency is also present in ~S(t), but it partakes of the nature of the chirp and does not contain a constant frequency that would produce a peak after Fourier transformation. In fact it is usual to filter out as much of the high frequency in ~S(t) as is possible without diminishing the ion signals, either by adjusting the time constant of the amplifier or by subsequent filtering.

A typical normal mode data acquisition might be to average 50 scans using an 0.2 ms pulse duration and 20 ms maximum drift time. This corresponds to a 1% duty cycle over the 1.00 s duration of the experiment. The normal mode amplifier needs a bandwidth of about 5000 Hz to pass the short ion pulses without broadening, and an A/D converter running at 5000 Hz to digitize the signal. A comparable FT mode acquisition would use a single 20–5020 Hz chirp lasting 1.00 s, giving a scan rate of 5000 Hzs$^{-1}$ with an overall 25% duty cycle (50% of the ion stream is lost at each of the two gates in succession). An ion with a 20 ms drift time would produce a frequency of 0.020 s×5000 Hz s$^{-1}$= 100 Hz in the interferogram, so the FT mode amplifier would need only a 100 Hz bandwidth. An A/D converter running at 512 Hz would be sufficient to digitize the signal, and after windowing and Fourier transformation the drift time spectrum out to 20 ms would be contained in the first 100 points of the transformed data. Because of the decreased bandwidth needed for the FT mode experiment, it is possible to disperse with the aperture grid 45. This is fortunate, because each gate or grid in the drift region D causes loss of ion signal.

There are two clear advantages of the FT mode compared to the normal mode. First, because the duty cycle of the FT mode is 25 times that of the normal mode the FT mode offers up to five times the S/N of the normal mode for equal data acquisition times. Second, the peak asymmetries due to reactions in the drift tube T simply disappear in the FT mode. This occurs because the FT mode needs a constant frequency difference between the ion-carried chirp and the second gate to generate a constant beat frequency. Ions that react during their transit of the drift space have no well-defined drift time and give incoherent signals at the second gate, adding only to the DC signal level and random background noise.

Figure 4:
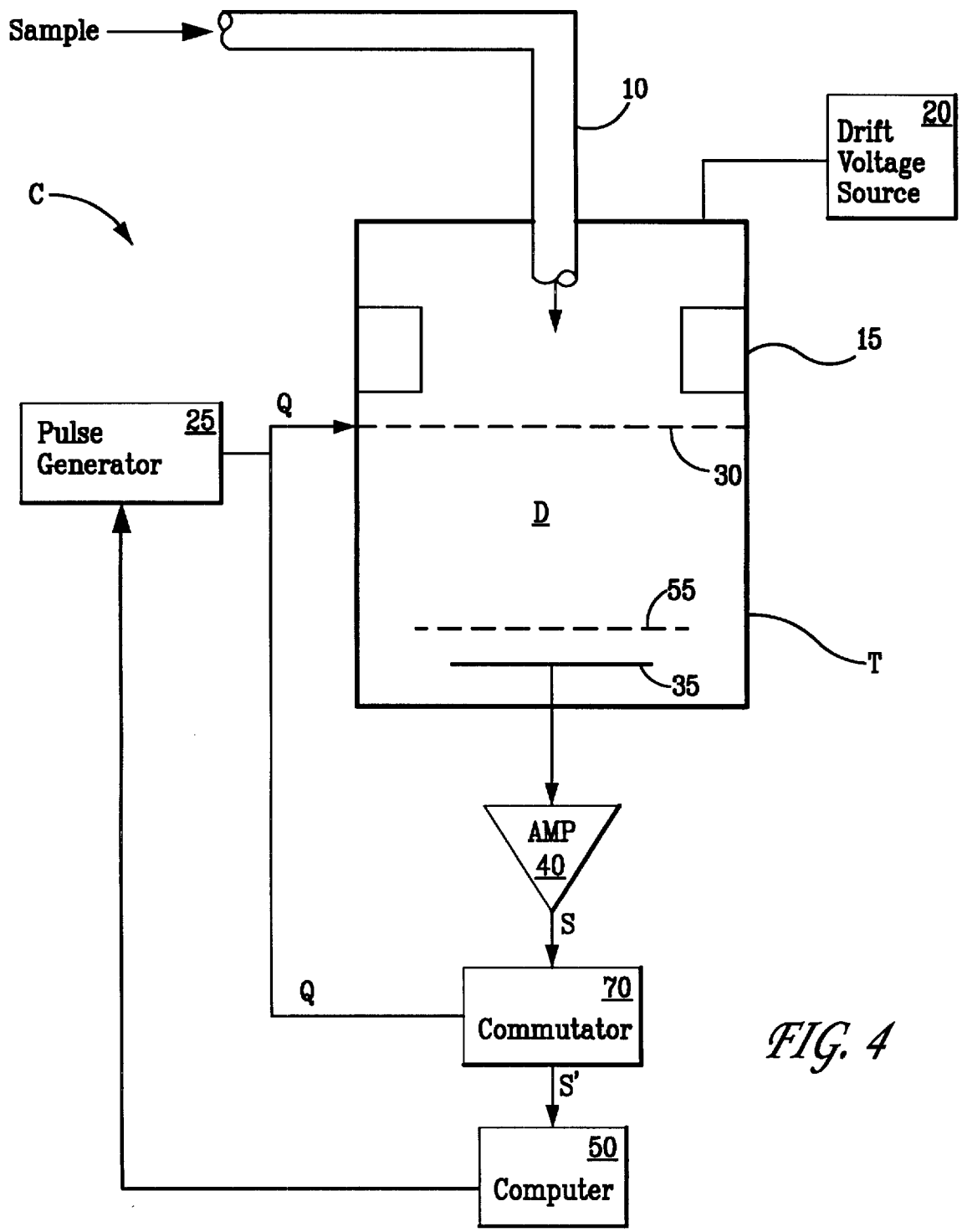
FIG. 4 represents a time-dispersive ion-mobility spectrometer according the present invention.

Looking now to FIGS. 4 and 5, the present invention will be described in more detail. As with the time dispersive ion mobility spectrometers previously described, the time-dispersive device of the present invention C includes a sample inlet 10, an ionizer 15, a drift tube T defining a drift region D, a high voltage source 20, an entrance gate 30, a pulse generator 25 (e.g. an Hewlett-Packard HP-33120A0) for controlling the follow of ions into the drift region D, an amplifier 40 and a computer based data acquisition system 50 for controlling the operation of time-dispersive device C. Additionally, the time-dispersive device C includes a commutator 70 for modulating an ion detection signal S developed by ion detector 35 and amplified by amplifier 40. Moreover, computer 50 includes a variety of software adapted to digitize a modulated ion detection signal S, display data, perform a Fast Fourier Transform ("FFT") of the signal S, and generating arbitrary waveforms for pulse generator 25 all of which will be discussed later.

Figure 2B:
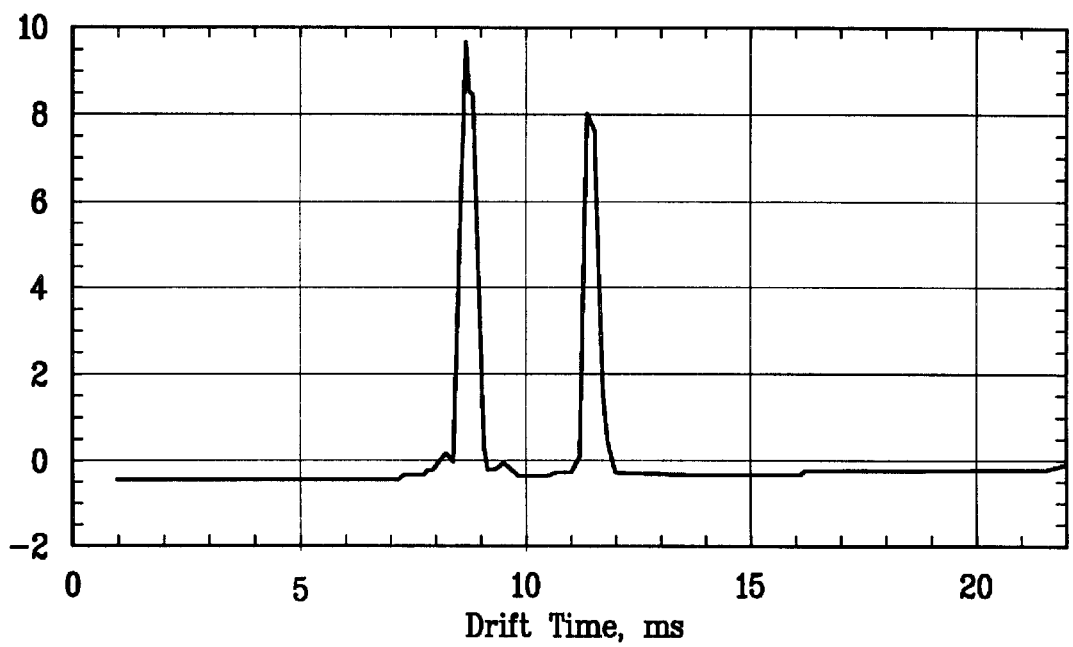
FIG. 2(b) represents the normalized time-of-flight spectra from a 0.5 second scan according to the present invention.

In operation, the flow of ions into the drift region D can be modulated by pulse generator 25. Preferably, pulse generator 25 develops a square wave although those skilled in the art will appreciate other wave forms can be used. Moreover, computer 50, causes pulse generator 25 to generate a swept frequency wave also known as a "chirp" signal Q. Similarly, chirp signal Q causes commutator 70 to gate or modulate the ion detection signal S. As with the FT time-dispersive device B described earlier, pulse generator 25 causes both entrance gate 30 and ion detection signal S to simultaneously be modulated by chirp signal Q. While chirp signal Q can be a square wave signal having linearly increasing frequency, those skilled in the art will appreciate that both the shape of the waveform and variation in frequency content can be varied. FIG. 2(b) provides a comparison of results of the present invention to three of existing devices as shown in FIG. 2(a).

Figure 5:
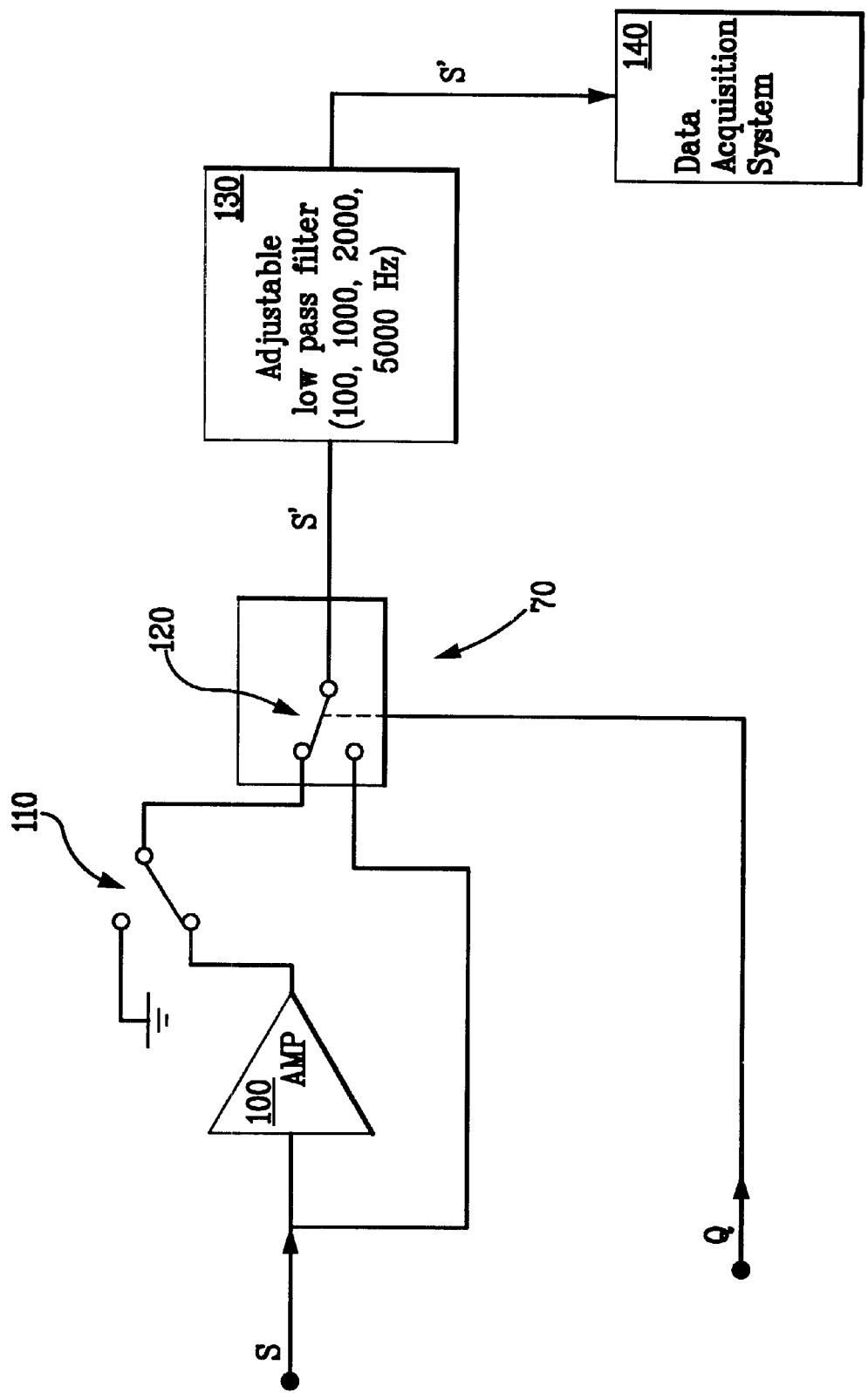
FIG. 5 represents one embodiment of commutator of the present invention.

One embodiment of the present invention includes novel electronic gating or modulation of the ion detection signal, S as depicted in FIG. 5 The output of the amplifier 100 is modulated by commutator 70 using chirp signal Q supplied by the pulse generator 25. Depending upon whether the chirp signal Q is at high state or low state, a fast analog switch 120 changes state to allow ion detection signal S to pass unchanged, or to be either grounded or inverted depending on the state of phase grounding switch 110. When the phase grounding switch 110 is set to the ground position, the commutator 70 emulates the action of a second gate physically located in the drift tube T. Depending of the phase of the chirp signal Q, commutator 70 either passes the ion detection signal S or blocks it leading to an overall 50% duty cycle. On the other hand when the phase grounding switch 110 is alternatively set to pass the output of the inverting fast amplifier 100, 50% of the ion steam passes through the drift tube T to contribute to the ion detection signal S, and thus offers an additional S/N advantage compared to throwing away half the signal at the second gate as done with conventional FT time dispersive devices.

The use of a fast analog switch 120 introduces transients into the interferogram which can compromise the operation of the data acquisition system 140. It turns out to be quite convenient to add bank of selectable low-pass filters 130 after fast analog switch 120. While necessary to eliminate transients, the selectable low-pass filter 138 is also very useful to block the higher frequencies in the interferogram and leave only lower frequencies corresponding to ion signals. The choice of (100, 1000, 2000, 5000) Hz cutoffs allows the FT mode operation to be performed at a variety of scan rates with a tailored passband.

Figure 6A:
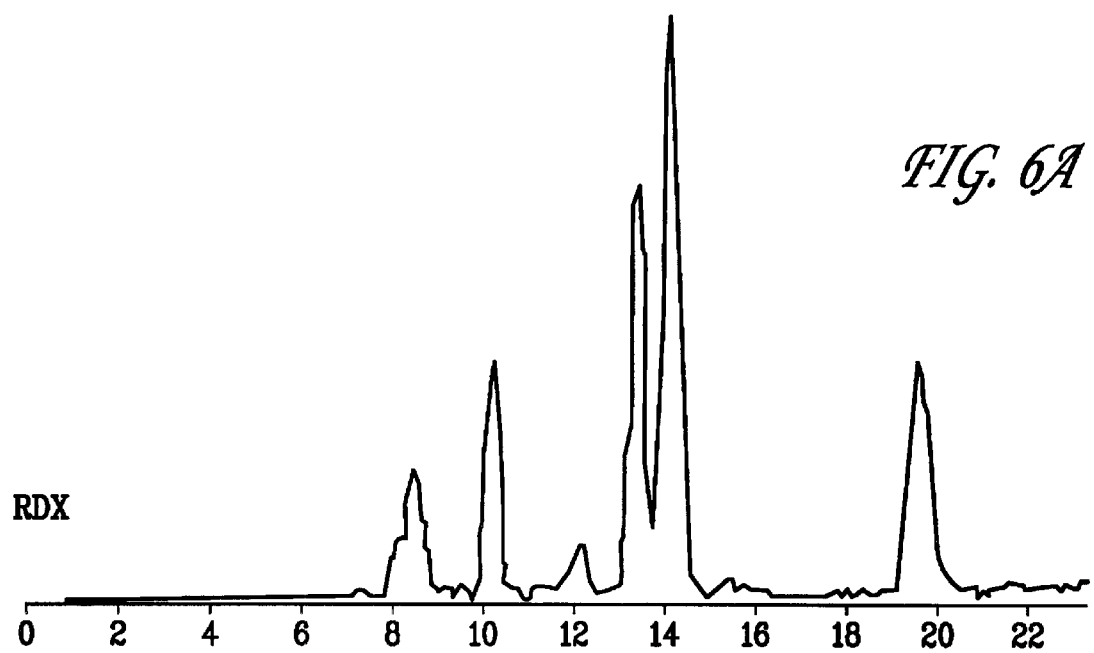
FIGS. 6(a,b) represent time-of-flight spectra obtained for RDX and TNT explosive material according to the present invention using a 0.5 second scan.
Figure 6B:
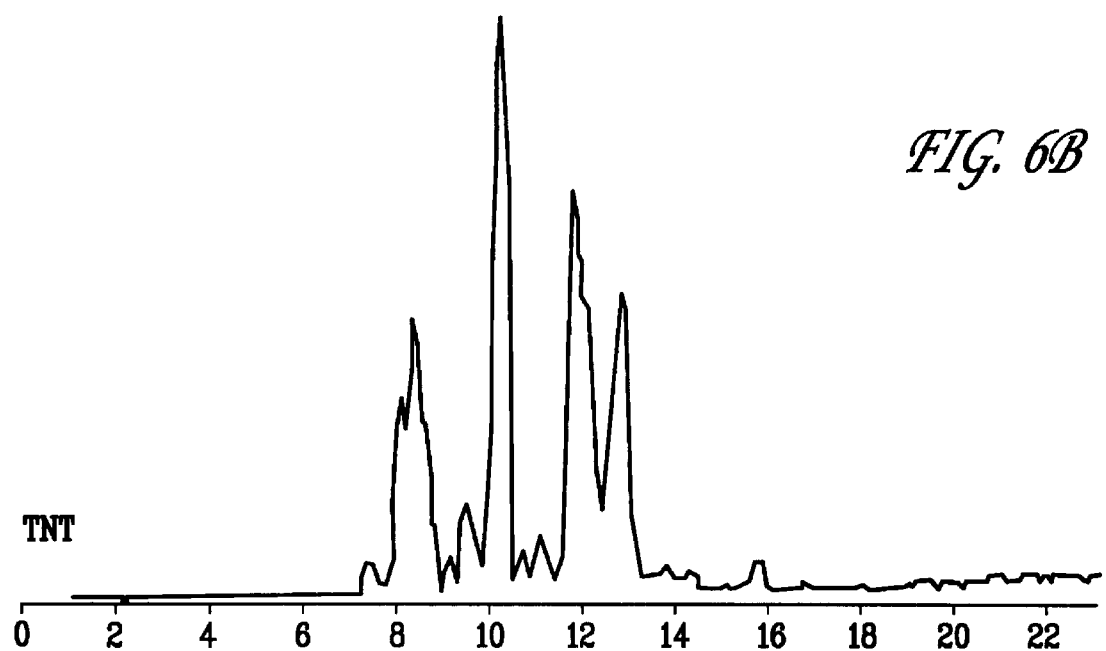
Figure 7A:
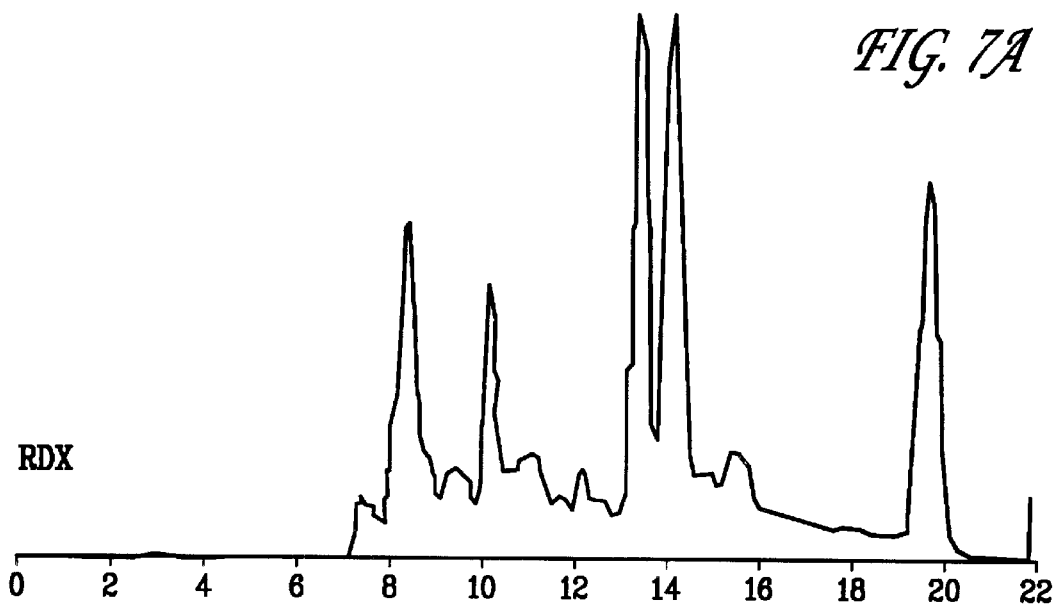
FIGS. 7(a,b) represent time-of-flight spectra obtained for RDX and TNT explosive material using the "averaged method" of time-dispersive spectroscopy acquired from a 4.2 second scan.
Figure 7B:
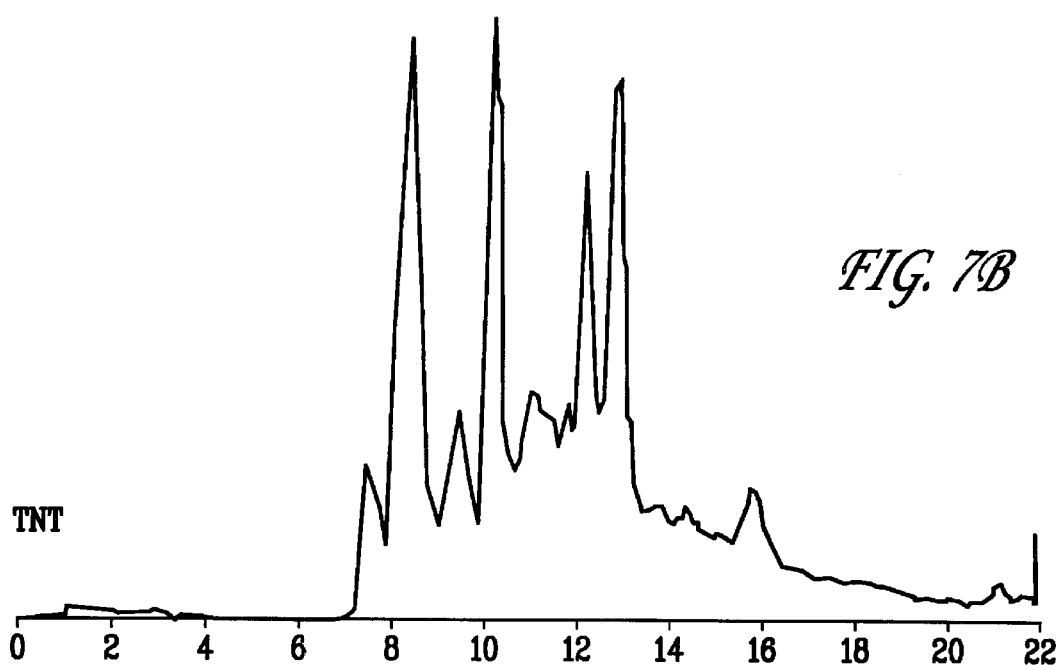

FIGS. 6(a,b) represent time-of-flight spectra for RDX and TNT explosive material, respectively, obtained according to the present invention. By comparison, FIGS. 7(a,b) represent time-of-flight spectra obtained for RDX and TNT explosive material, respectively, using the "averaged method" of times-dispersive spectroscopy. It can be seen that the fronting and tailing problems previously described have largely been resolved as well as a much improved S/N. Moreover, the differences in acquisition times (i.e. 0.5 seconds versus 4.2 seconds) clearly demonstrate that not only can better S/N be obtained; but that, it can be obtained in less time. Thus, the present method provides time-of-flight spectra having increased S/N and requires less time to acquire than conventional approaches to qualitative and quantitative analyses thus more useful results. It should be noted that no comparison of the present method has been made with existing FT methods. As explained earlier, because differences in the physical structure of the devices themselves, most notably two's gates versus one gate, such comparisons cannot be meaningfully done.

To employ the invention with time-dispersive devices other than ion mobility spectrometers, it is only necessary to modify the rise time characteristics of the commutator 70 components to accommodate the rise time characteristics of the particular device. In particular, an commutator 70 gate for TOF spectrometers would need a very fast analog switch.

While the specific examples used to illustrate this invention are all derived from ion mobility spectrometry (IMS), it will be clear that the invention can be employed in exactly the same fashion with any time-dispersive device. By time-dispersive device, we mean an apparatus which can separate the constituents of a multi-component mixture on the basis of the differing velocities of the constituents through the separation space or medium of the instrument. The separation space may be the drift tube of an IMS, the flight tube of a TOF MS, a capillary GC or electrophoresis column, and the like.

What is claimed is:

1. A method of time dispersive spectroscopy, comprising:
   a) ionizing a sample to produce ionized molecules;
   b) modulating the flow of ionized molecules into a drift region of a spectrometer;
   c) detecting the ionized molecules at a detector, and producing an ion detection signal;
   d) directing said ion detection signal into a commutator, said commutator comprising a high speed switch;
   e) modulating the high speed switch between a first state and a second state to provide a modulated ion detection signal, said high speed switch gating the ion detection signal by passing the ion detection signal when said high speed switch is in said first state or blocking the ion detection signal when said high speed switch is in said second state; and
   f) assaying the chemical constituents of the sample from the modulated ion detection signal.

2. The method of claim 1, wherein the flow of ionized molecules into the drift region and the ion detection signal are modulated in a like manner.

3. The method of claim 2, wherein such modulation is of varying frequency and duration.

4. The method of claim 1, further including the step of transforming the ion detection signal into a frequency domain signal.

5. The method of claim 1, further includes obtaining a frequency difference between the modulated ion detection signal and the modulation rate.

6. The method of claim 1, wherein the flow of ions is modulated with a signal of varying frequency and duration.

7. The method of claim 1, wherein the ion detection signal is modulated with a signal of varying frequency and duration.

8. The method of claim 6, wherein the signal is a swept frequencies signal which varies frequency linearly with time.

9. The method of claim 7, wherein the signal is a chirp signal which varies linearly with time.

10. A time-dispersive spectrometer, comprising:
    a) means for ionizing a sample;
    b) means for modulating the flow of ions into a drift region of the spectrometer:
    c) an ion detector for detecting the ions after they have traversed the drift region, said ion detector producing an ion detection signal; and
    d) means for modulating the ion detection signal, wherein said modulation means comprises a high speed switch alternating between first and second states, and wherein said ion detection signal is passed when said high speed switch is in said first state or blocked when said high speed switch is in said second state.

11. The spectrometer of claim 10, wherein said means for modulating the flow of ions includes a swept wave generator of varying frequency and duration.

12. The spectrometer of claim 10, wherein said means for modulating the ion detection signal further includes means for obtaining a frequency domain signal for assaying the constituents of the sample.

13. The spectrometer of claim 10, further includes means for obtaining a time domain signal for assaying the chemical constituents of the sample.

14. The spectrometer of claim 12, further includes means for transforming the frequency domain signal into a time domain signal for assaying the chemical constituents of the sample.

15. The spectrometer of claim 11, wherein said means for modulating the flow of ions and includes means for linearly varying both the duration and frequency of flow of ions.

16. The spectrometer of claim 11, wherein said means for modulating the ion detection signal includes means for linearly varying both the duration and frequency of the ion detection signal.

17. The spectrometer of claim 10, wherein the flow of ions and ion detection signal are modulated in a like manner.

* * * * *